US00PP14291P29

(12) United States Plant Patent
Koeze

(10) Patent No.: US PP14,291 P2
(45) Date of Patent: Nov. 11, 2003

(54) BEGONIA PLANT NAMED 'BBPICOTEE'

(50) Latin Name: *Begonia elatior*
Varietal Denomination: Bbpicotee

(75) Inventor: Bert Koeze, Nieuw Vennep (NL)

(73) Assignee: Begonia Breeders Association B.V. (NL)

( * ) Notice: Subject to any disclaimer, the term of this patent is extended or adjusted under 35 U.S.C. 154(b) by 0 days.

(21) Appl. No.: 10/209,287

(22) Filed: Jul. 31, 2002

(51) Int. Cl.[7] ..... A01H 5/00
(52) U.S. Cl. ..... Plt./348
(58) Field of Search ..... Plt./348

*Primary Examiner*—Bruce R. Campell
*Assistant Examiner*—Michelle Kizilkaya
(74) *Attorney, Agent, or Firm*—Webb Ziesenheim Logsdon Orkin & Hanson, P.C.

(57) ABSTRACT

A new and distinct begonia plant with pink-red colored double flowers.

1 Drawing Sheet

Classification: *Begonia elatior.*
Varietal denomination: 'BBPICOTEE'.

BACKGROUND OF THE INVENTION

The present invention comprises a new and distinct cultivar of *Begonia Elatior* known by the varietal name 'BBPICOTEE'. The new variety was discovered in a planned breeding program as a single plant in a group of plants of the parent cultivar in Amstelveen, Netherlands, in 1998. The new variety is a result of cross breeding of a variety of *Begonia tuberosum* (female) and a variety of *Begonia socotrana* (male). The new variety has more petals, larger leaves, and bigger flowers than 'LOUISE' (unpatented). The new variety was first asexually reproduced by cuttings in Aalsmeer in 1999. The new variety has been trial and field tested and has been found to retain its distinctive characteristics and remain true to type through successive propagations. 'Bbpicotee' differs from both parent plants in terms of size, shape and growth habit.

The new variety, when grown in a glass greenhouse has a response time for rooting from a terminal cutting of 14 days.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions by cuttings in a 20° C. shaded greenhouse on a 12 week old plant grown in a 13 cm diameter pot. Color references are primarily to The R.H.S. Colour Chart of The Royal Horticultural Society of London.

PLANT

Form: Upright, compact.
Height:
*From media surface to top of leaves.*—18 cm.
*From media surface to top of flowers.*—22 cm.
Width: 25 cm.

Time to initiate roots: About 14 days.
Time to develop roots: 35 days.
Rooting habit: Fine, fibrous, free branching.
Lateral branches:
*Number.*—4.
*Color.*—145A.
Leaves:
*Arrangement.*—Alternate.
*Shape.*—Asymmetrical ovate overall with acute apex and cordate base.
*Size.*—9 cm long; 8 cm wide.
*Margin.*—Doubly serrated.
*Quantity.*—8 per lateral branch.
*Texture.*—Smooth; velvety.
*Color.*—139A.
*Venation.*—Color: Upper surface: 139A. Lower surface: 138B.
*Petiole.*—Diameter: 4 mm. Color: 145A.
*Stipules.*—2 per leaf, 1 cm long. Overall shape: Asymmetrical, pointed. Apex shape: Acute. Base shape: Straight. Margin: Entire. Color: Upper surface: 145A. Lower surface: 145A.

FLOWERS

Habit: Small.
Natural flowering season: Year round.
Flowering longevity: 4 weeks on the plant.
Flowers:
*Arrangement.*—Compound, not aborted.
*Cyme diameter.*—7 cm.
*Number of flowers per cyme.*—6.
*Aspect.*—Flat to cupped.
*Shape.*—Oval to round.
*Fragrance.*—None.
*Size.*—5 cm in diameter; 1 cm deep.
*Number of flowers per plant.*—30.
Flower buds:
*Shape.*—Oval.
*Size.*—1.5 cm long; 2 cm wide.
*Color.*—55D.
*Rate of flower opening.*—3–4 days.
Petals:
*Arrangement.*—Semi-double to single.
*Shape.*—Rounded to obovate.

*Apex shape.*—Obtuse.
*Base shape.*—Cuneate.
*Margin.*—Entire.
*Quantity per flower.*—15–20.
*Size.*—Length: 3 cm. Width: 4 cm.
*Texture.*—Smooth.
*Color.*—Upper surface: 55D with margin of 56D. Lower surface: 55D.

Peduncles:
*Angle.*—30–40° from vertical.
*Strength.*—Strong.
*Length.*—8 cm.
*Color.*—145A.

Pedicels:
*Angle.*—30–40°.
*Strength.*—Strong.
*Length.*—2–3 cm.
*Color.*—146D.

Bracts:
*Arrangement.*—Opposite.
*Shape.*—Broadly cordate.
*Apex shape.*—Acute.
*Margin.*—Entire.
*Color.*—Upper surface: 145A. Lower surface: 145A.

REPRODUCTIVE ORGANS

Stamens: None observed.
Pistils: None observed.
Disease resistance: Mildew tolerant.
Seed production: Seed production has not been observed as reproductive organs are not formed.

I claim:

1. A new and distinct variety of begonia plant substantially as shown and described.

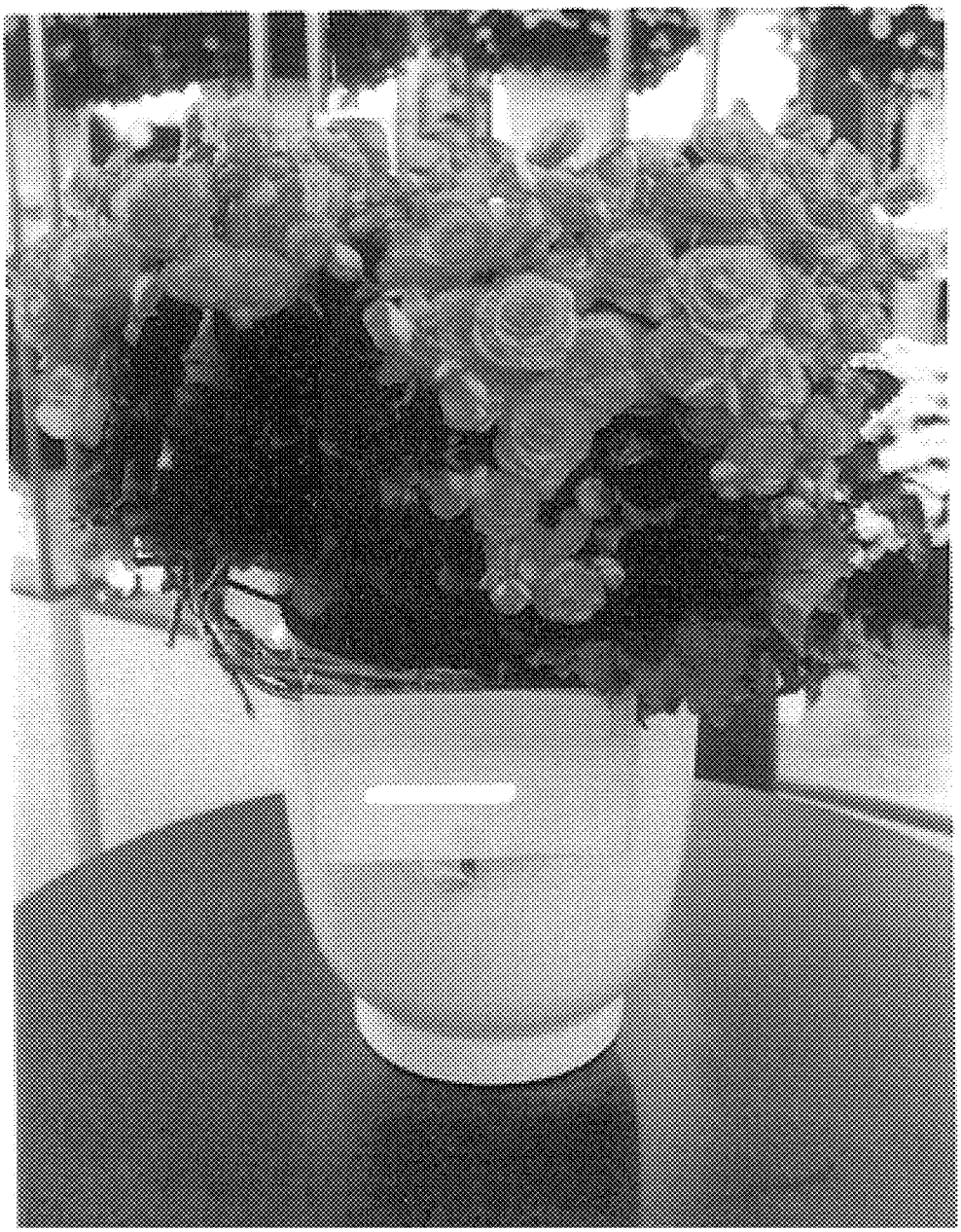

* * * * *